(12) United States Patent  
Sharpless

(10) Patent No.: US 9,173,627 B2  
(45) Date of Patent: Nov. 3, 2015

(54) COMPUTED TOMOGRAPHY (CT) DATA ACQUISITION

(75) Inventor: Ronald B. Sharpless, Cleveland, OH (US)

(73) Assignee: Koninklijke Philips N.V., Eindhoven (NL)

(*) Notice: Subject to any disclaimer, the term of this patent is extended or adjusted under 35 U.S.C. 154(b) by 74 days.

(21) Appl. No.: 13/978,596

(22) PCT Filed: Jan. 6, 2012

(86) PCT No.: PCT/IB2012/050079  
§ 371 (c)(1),  
(2), (4) Date: Jul. 8, 2013

(87) PCT Pub. No.: WO2012/095773  
PCT Pub. Date: Jul. 19, 2012

(65) Prior Publication Data  
US 2013/0287165 A1   Oct. 31, 2013

Related U.S. Application Data

(60) Provisional application No. 61/431,081, filed on Jan. 10, 2011.

(51) Int. Cl.  
*A61B 6/03* (2006.01)  
*A61B 6/00* (2006.01)

(52) U.S. Cl.  
CPC .............. *A61B 6/5294* (2013.01); *A61B 6/032* (2013.01); *A61B 6/54* (2013.01); *A61B 6/545* (2013.01); *A61B 6/547* (2013.01)

(58) Field of Classification Search  
CPC ................................. A61B 6/545; A61B 6/547  
USPC ........................................................ 378/19, 4  
See application file for complete search history.

(56) References Cited

U.S. PATENT DOCUMENTS

| | | | |
|---|---|---|---|
| 5,175,754 A * | 12/1992 | Casey et al. | 378/4 |
| 5,432,339 A | 7/1995 | Gordon et al. | |
| 6,169,778 B1 | 1/2001 | Schmidt et al. | |
| 6,574,301 B1 | 6/2003 | Jansen | |
| 7,278,786 B2 | 10/2007 | Fiedler et al. | |

* cited by examiner

*Primary Examiner* — David J Makiya  
*Assistant Examiner* — Dani Fox

(57) ABSTRACT

An imaging system (100) includes a stationary gantry (102), a rotating gantry (104), a radiation source (110), and a detector array (112). The detector array detects radiation for a plurality of integration periods during a rotating gantry revolution, the plurality of integration periods corresponds to different angular position ranges, and the detector array generates a signal indicative of the detected radiation respectively for the plurality of integration periods. The system further includes an integration period controller (118) that generates an integration period timing signal that includes timing for a start of each of the integration periods for a revolution of the rotating gantry based at least on a time duration of a previous revolution of the rotating gantry around the examination region, wherein the integration timing signal is used trigger the plurality of integration periods.

15 Claims, 7 Drawing Sheets

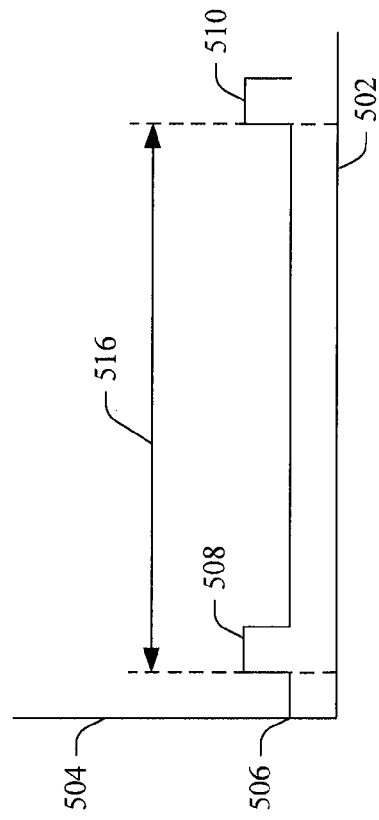
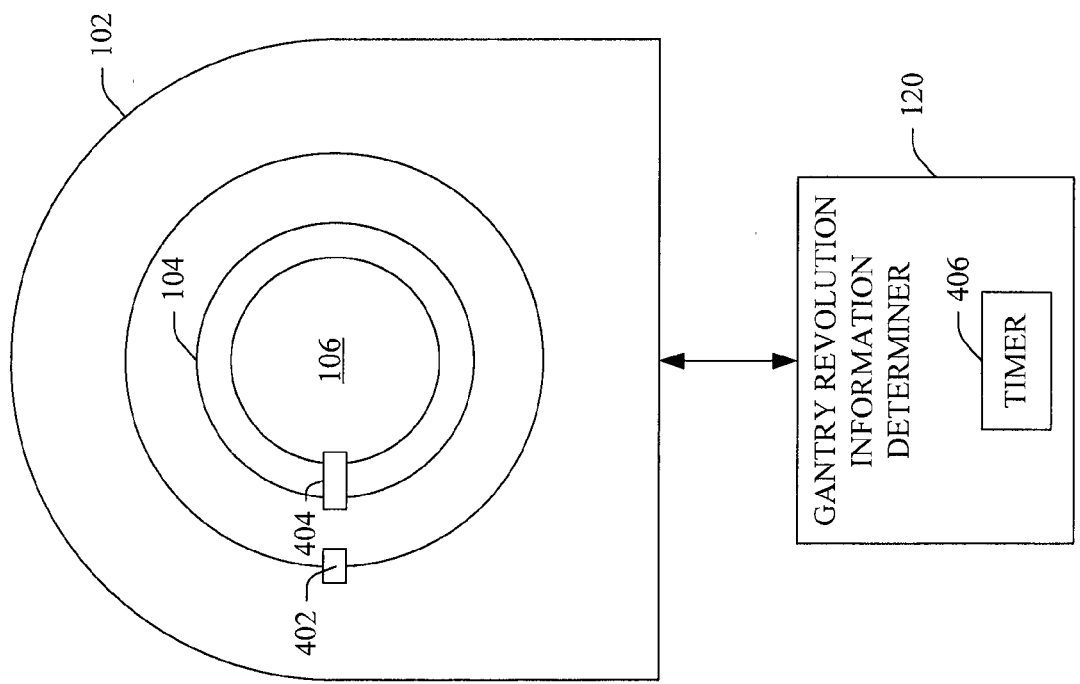
FIGURE 5
FIGURE 4

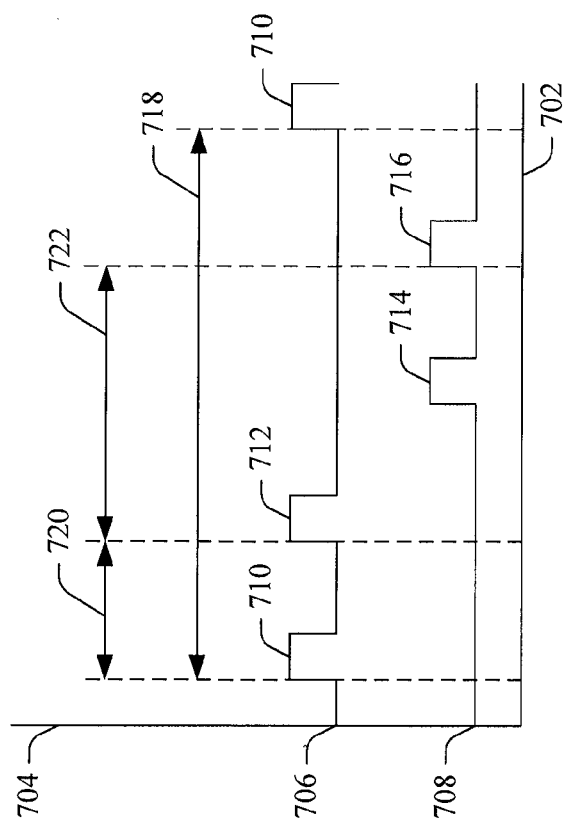
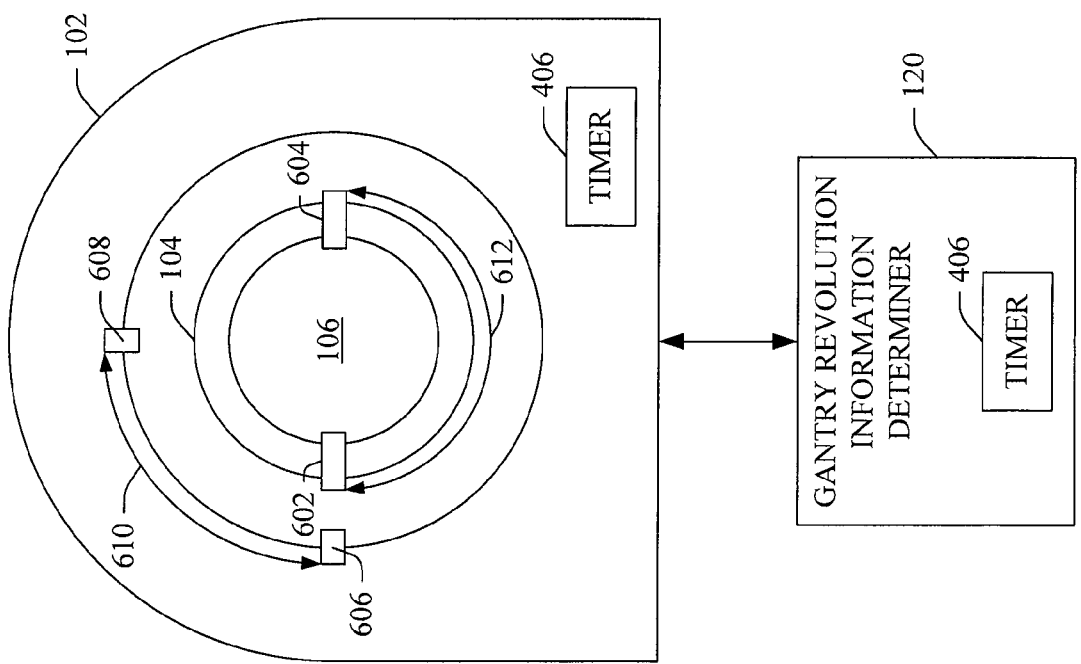
FIGURE 7
FIGURE 6

COMPUTED TOMOGRAPHY (CT) DATA ACQUISITION

CROSS REFERENCE TO RELATED APPLICATIONS

This application is a national filing of PCT application Ser. No. PCT/IB2012/050079, filed Jan. 6, 2012, published as WO 2012/0095773 A2 on Jul. 19, 2012, which claims the benefit of U.S. provisional application Ser. No. 61/431,081 filed Jan. 10, 2011, which is incorporated herein by reference.

FIELD OF THE INVENTION

The following generally relates to imaging system data acquisition and is described with particular application to computed tomography (CT).

BACKGROUND OF THE INVENTION

A computed tomography (CT) scanner includes a rotating portion rotatably supported by a stationary portion. The rotating portion supports an x-ray tube, which emits radiation that traverses an examination region and a portion of an object or subject therein, and a detector array that detects radiation traversing the examination region and generates projection data indicative of the detected radiation. A reconstructor reconstructs the projection data and generates volumetric image data indicative of the portion of the object or subject in the examination region. One or more images can be generated based on the image data.

The detector array includes detector pixels that convert detected x-ray photons into electrical signals indicative thereof. For each revolution of the rotating gantry, the detector pixels detect and convert x-ray photons for a plurality of integration periods, each corresponding to a different angular position range. The time duration of an integration period depends on the rotating gantry rotation speed and the number integration periods for each revolution of the scan. With an integrating detector array, at the beginning of each integration period, the integrators for the detector pixels are reset, and then the integrators receive and integrate the electrical signals over the integration period. The integrated signals form the projection data for that integration period.

The reconstructor processes projection data for a given integration period as corresponding to a particular angular position range. However, if the integration period timing with respect to the angular position range is not accurate, then, in actuality, the projection data corresponds to a different angular position range, and this may result in degraded image quality of the reconstructed image data. Unfortunately, there is a natural rotating gantry position error in which the dominant disturbance of the rotating gantry velocity is imbalance, which is a function of rotating gantry angle, and the amount of angular error due to the imbalance is a function of the inverse of the cube of the rotation speed.

A highly accurate large diameter rotating gantry position determining apparatus has been used to determine the actual position of the rotating gantry, which has been used to synchronize the integration period timing and rotating gantry angular position range. Such an apparatus has included a high resolution encoder and resolver, supporting electronics, a power supply, and a slip ring to transfer data between the rotating and stationary portions of the scanner. Unfortunately, such apparatuses generally are complex and expensive, and increase the overall cost of the scanner.

SUMMARY OF THE INVENTION

Aspects of the present application address the above-referenced matters and others.

According to one aspect, an imaging system includes a stationary gantry and a rotating gantry rotatably supported by the stationary gantry and configured to rotate around an examination region. The system further includes a radiation source, carried by the rotating gantry, that is configured to emit radiation that traverses the examination region, and a detector array, carried by the rotating gantry and located opposite the radiation source across the examination region, that detects radiation that traverses the examination region. The detector array detects radiation for a plurality of integration periods during a rotating gantry revolution, the plurality of integration periods corresponds to different angular position ranges, and the detector array generates a signal indicative of the detected radiation respectively for the plurality of integration periods. The system further includes an integration period controller that generates an integration period timing signal that includes timing for a start of each of the integration periods for a revolution of the rotating gantry based at least on a time duration of a previous revolution of the rotating gantry around the examination region, wherein the integration timing signal is used to trigger the plurality of integration periods.

According to another aspect, a method includes generating an integration period timing signal including timing of a plurality of data acquisition integration periods for a revolution of a rotating gantry of an imaging system, wherein the integration period timing signal is generated based at least on a time duration of a previous revolution of the rotating gantry.

According to another aspect, a method includes correcting predicted integration period data acquisition timing, in connection with a rotating gantry of an imaging system, for rotating gantry imbalance.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

FIG. 4 schematically illustrates an example imaging system utilizing a single and a flag to facilitate determining an IP timing signal.

FIG. 5 shows an example timing diagram of the sensor of FIG. 4.

FIG. 6 schematically illustrates an example imaging system utilizing multiple sensors and multiple flags to facilitate determining an IP timing signal and a correction thereto.

FIG. 7 shows an example timing diagram of the sensors of FIG. 6.

DETAILED DESCRIPTION OF EMBODIMENTS

Figure 1:
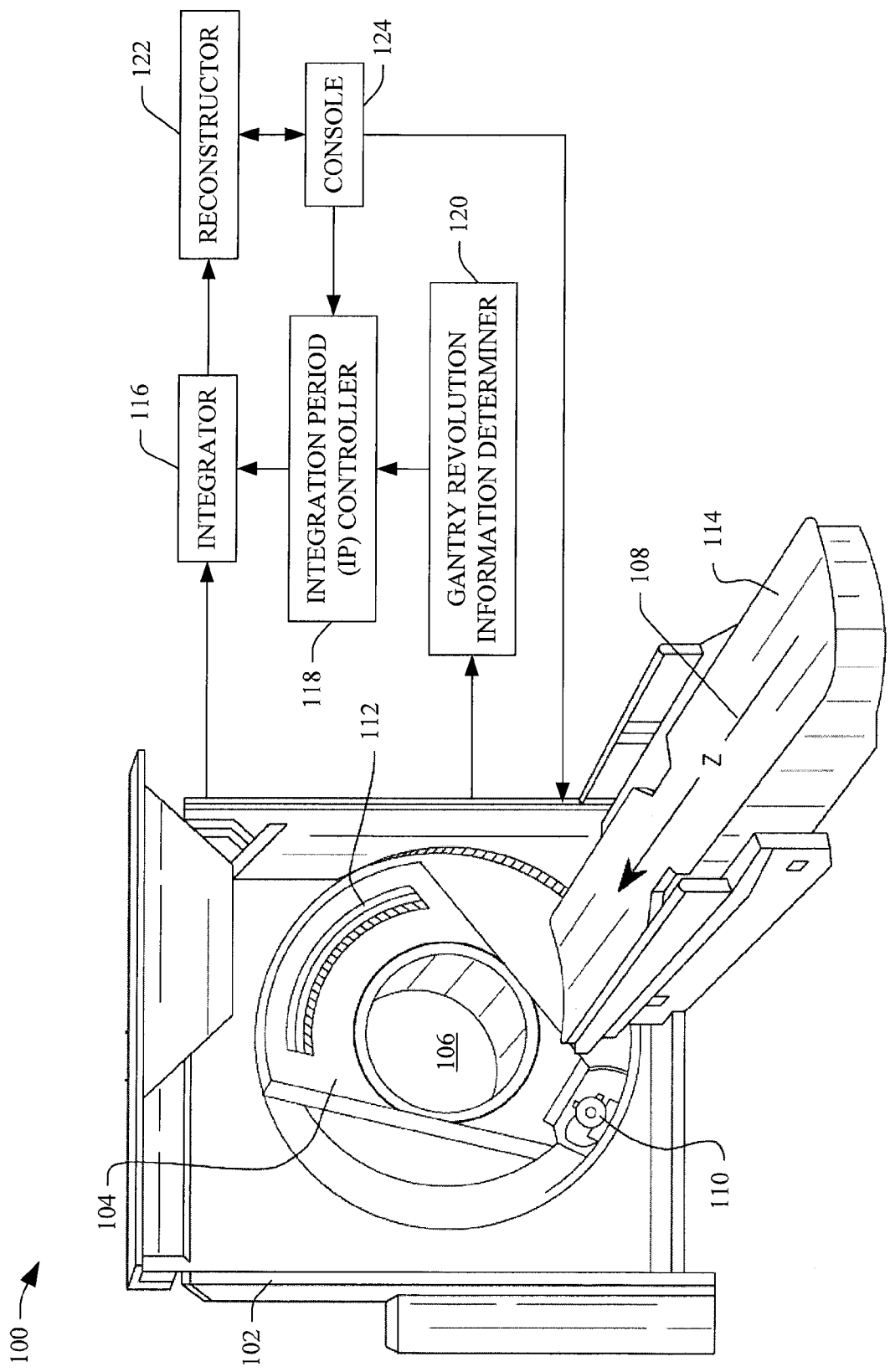
FIG. 1 schematically illustrates an imaging system in connection with an integration period controller.

FIG. 1 schematically illustrates an imaging system such as a computed tomography (CT) scanner 100. The scanner 100 includes a stationary gantry 102 and a rotating gantry 104, which is rotatably supported by the stationary gantry 102. The rotating gantry 104 rotates around an examination region 106 about a longitudinal or z-axis 108 one or more times for one or more data acquisition cycles. A patient support 114, such as a couch, supports a patient in the examination region 106.

A radiation source 110, such as an x-ray tube, is supported by and rotates with the rotating gantry 104 around the examination region 106. The radiation source 110 emits radiation that is collimated by a source collimator to produce a generally fan, wedge, or cone shaped radiation beam that traverses the examination region 106. A radiation sensitive detector array 112 includes a one or two dimensional array of detector pixels that respectively detect radiation that traverses the examination region 106 and generate electrical signals (e.g., a current or a voltage) indicative of the detected radiation.

An integrator 116, which includes one or more sub-integrators, such as a sub-integrator for each detector pixel of the detector array, integrates the electrical signals from the detector pixels respectively for a plurality of integration periods (views, projections, etc.), each integration period corresponding to different angular position range over a revolution of the rotating gantry 104, for one or more revolutions of the rotating gantry 104 during data acquisition, producing projection data.

An integration period (IP) controller 118 controls the integrator 116. By way of example, the illustrated IP controller 118 triggers a reset of the integrator 116 at the start of each integration period, along with transfer of any the integrated signal for the previous integration period.

As described in greater detail below, the IP controller 118 determines when to reset the integrator 116 and produces a signal that resets the integrator 116 based on information about a previous revolution of the rotating gantry 104 obtained before (e.g., pre-scan) and/or during scanning. In the illustrated embodiment, a gantry revolution information determiner 120 determines such information. In one instance, the determined gantry revolution information allows for synchronizing integration period (IP) timing (i.e., integrator resets) with the angular position range of the rotating gantry 104 with and/or without correcting the IP timing signal for rotating gantry imbalance.

It is to be understood that such synchronization can be achieved without using an additional rotating gantry position determining apparatus. As such, the IP controller 118 may facilitate maintaining or reducing overall scanner cost, for example, by mitigating incorporation of a highly accurate rotating gantry position determining apparatus into the imaging system 100, while achieving a predetermined image quality (e.g., a given spatial resolution and/or mitigating introduction of artifact caused by timing inaccuracies), relative to a configuration in which the IP controller 118 is omitted. Of course, a rotating gantry position determining apparatus can also be used.

A reconstructor 122 reconstructs the projection data and generates volumetric image data indicative of the examination region 106. A general purpose computing system serves as an operator console 124, and includes an output device such as a display and an input device such as a keyboard, mouse, and/or the like. Software resident on the console 124 allows the operator to control the operation of the system 100, for example, allowing the operator to initiate scanning, etc.

Although the integrator 116 and IP controller 118 are shown as blocks separate from the detector array 112, it is to be appreciated that one or more of the integrator 116 or the IP controller 118 can be part of the detector array 112. Furthermore, the gantry revolution information determiner 120 can be part of the rotating and/or stationary gantries 104 and 102.

Moreover, it is to be understood that at least a sub-portion of the IP controller 118 can be implemented via one or more processors executing one or more computer readable instructions encoded on computer readable storage medium. Additionally or alternatively, the one or more computer readable instructions can be carried by a signal, a carrier wave or the like.

Figure 2:
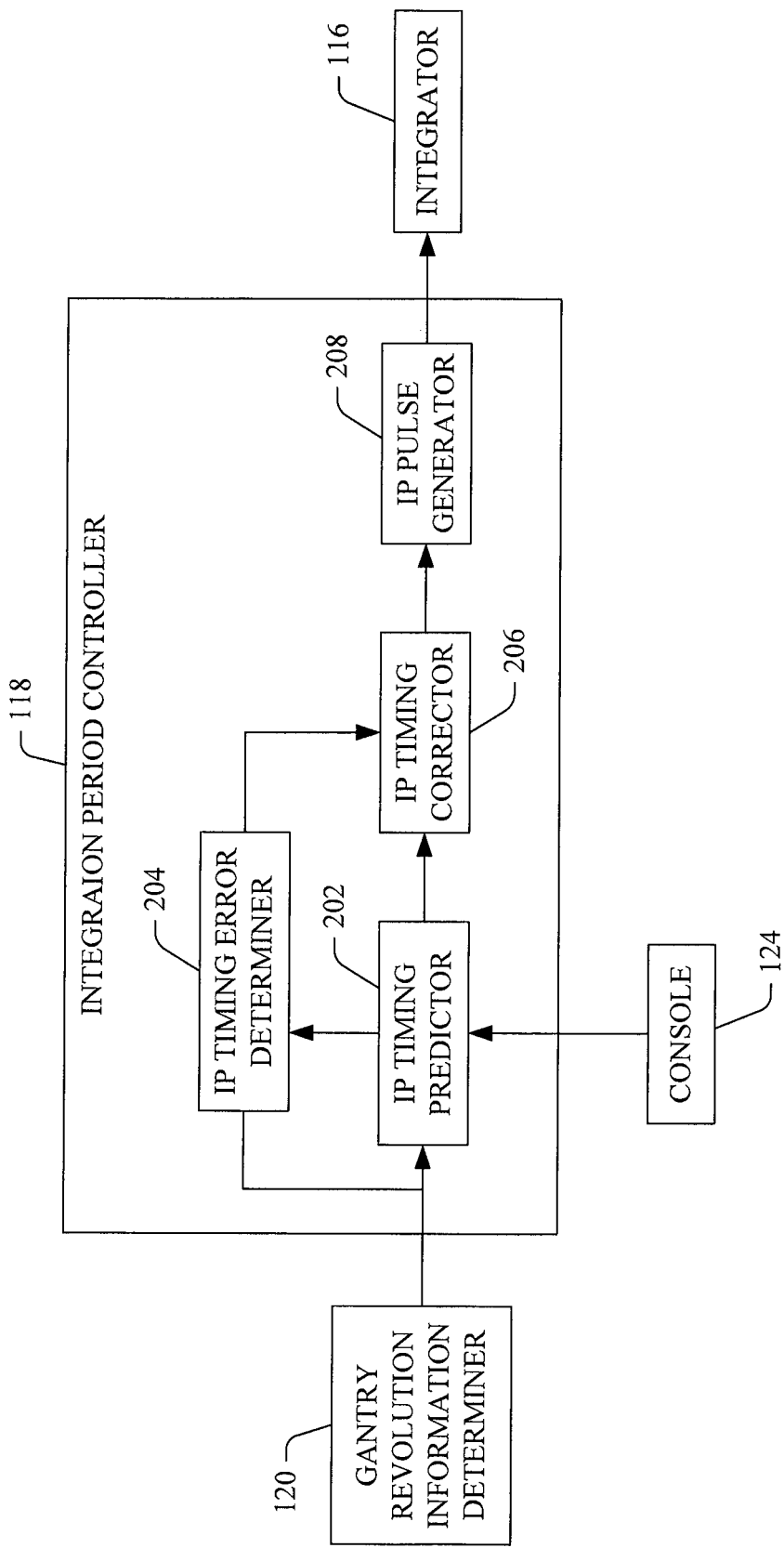
FIG. 2 schematically illustrates an example integration period controller.

FIG. 2 illustrates an example of the IP controller 118 in connection with the gantry revolution information determiner 120, the console 124 and the integrator 116.

The gantry revolution information determiner 120 determines timing information about a revolution of the rotating gantry 104. Generally, a suitable gantry revolution information determiner 120 may include one or more sensors affixed to the rotating gantry 104 (or the stationary gantry 102) and one or more flags affixed to the stationary gantry 102 (or rotating gantry 104) in which the sensor(s) and the flag(s) are arranged so that there is relative movement there between when the rotating gantry 104 rotates, and a sensor detects a flag rotating passed the sensor and generates a signal indicative of the detected flag. A timer or the like can be used determine an amount of time between detection of the flags for one or more of the sensors. A non-limiting example implementation is described in greater detail below.

An IP timing predictor 202 predicts an IP timing signal for a particular scan. In the illustrated embodiment, the IP timing predictor 202 predicts the IP timing signal for a revolution based on gantry revolution information for a previous revolution and information indicative of the rotation speed of the rotating gantry 104 and a number of integration periods (IPs) for a scan protocol of interest. By way of example, in one instance the IP timing predictor 202 divides the amount of time for the previous revolution by the rotation speed and the number of IPs to calculate an IP timing signal indicative of a plurality of equally angularly spaced IPs. Suitable IP time durations or widths include, but are not limited to, time widths in a range of about fifty microseconds (50 µs) to about five hundred microseconds (500 µs). Of course, other IP time widths are also contemplated herein.

In the illustrated embodiment, the IP timing predictor 202 can receive the gantry rotation speed and number of IPs information from the console 124. Where scanner 100 includes protocols with the same gantry rotation speed and number of IPs, the gantry rotation speed and number of IPs can additionally or alternatively be stored in memory in and/or accessible to the IP controller 118. In another embodiment, the IP controller 118 additionally or alternatively stores and/or can access memory which stores a mapping (e.g., a look up table (LUT)) between particular scan protocols and the gantry rotation speed and number of IPs for each scan protocol, and uses the mapping to determine the gantry rotation and the number of IPs for a protocol identified, for example, in information from the console 124 and/or other component.

An IP timing error determiner 204 generates an IP error signal indicative of fluctuations in rotating gantry 104 rotational velocity, for example, due to rotating gantry 104 imbalances and/or otherwise, which may result in a timing inaccuracy between the predicted IP timing signal and the actual angular position range of the rotating gantry 104. In the illustrated embodiment, the IP timing error determiner 204 generates the error signal based on the information from the gantry revolution information determiner 120 and/or the IP timing predictor 202. In one instance, the IP timing error determiner 204 determines a difference between the predicted IP timing and measured actual IPs for a sub-set of angular positions, determines error values based on the differences, and uses the error values to generate a correction to the predicted IP signal. An example implementation of the IP timing error determiner 204 is described in greater detail below.

An IP timing corrector 206 corrects the predicted IP timing signal from the IP timing predictor 202 based on the IP timing error signal from the IP timing error determiner 204. In one non-limiting embodiment, the IP timing corrector 206 may simply sum or otherwise combine the IP timing signal and the IP timing error signal.

An IP pulse generator 208 generates integrator reset pulses, based on the corrected IP timing signal, which resets the integrator 116 for each integration period for each rotation of the rotating gantry 104 during scanning. In the illustrated embodiment, the IP pulse generator 208 generates a serial stream of pulses, which triggers data transfer from and reset of the integrator 116. The output of the integrator 116 produces the projection data that is reconstructed by the reconstructor 122 as discussed above.

Variations are contemplated.

Where the IP error is within a predetermined range (e.g., fifty (50) arc seconds or less), the IP timing error determiner 204 and the IP timing corrector 206 can be omitted or not utilized. In this instance, the timing signal from the predicted IP timing predictor 202 is provided to and used by the IP pulse generator 208 to produce the integrator reset pulses.

Figure 3:
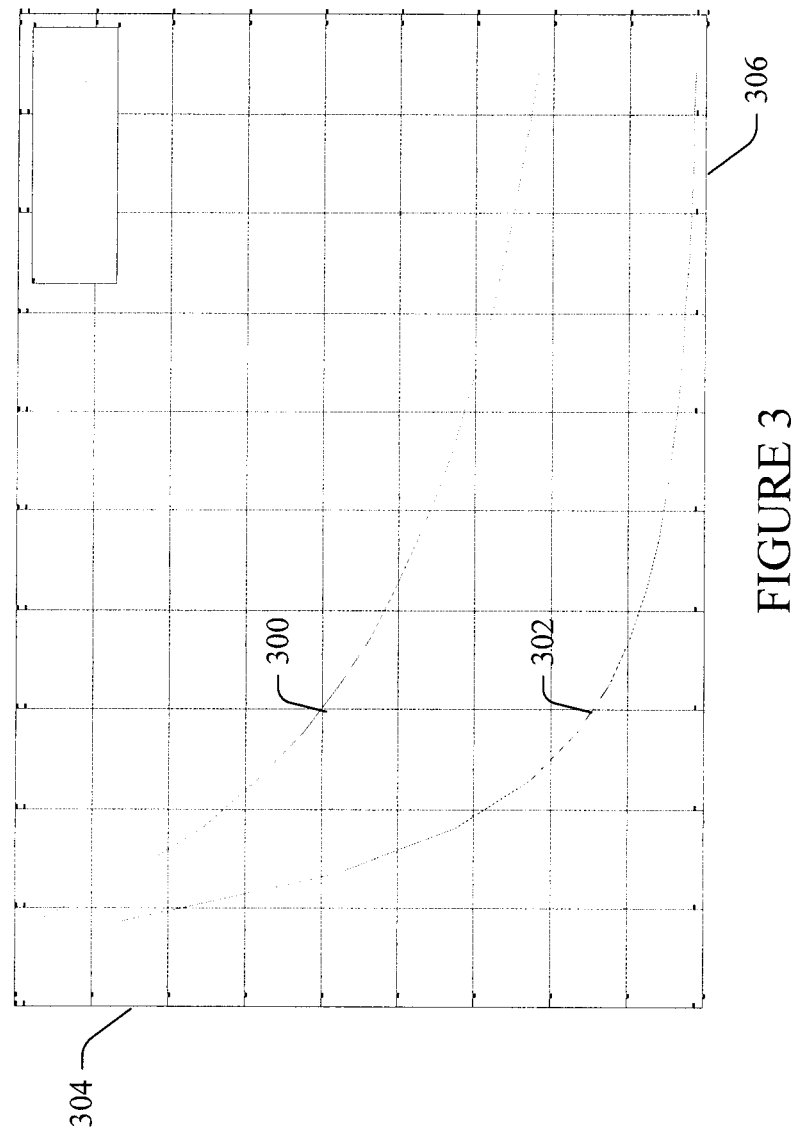
FIG. 3 shows an example plot of IP timing and IP error as a function of rotating gantry rotation speed.

FIG. 3 shows examples of an IP timing curve 300 and an IP error curve 302, as a function of rotating gantry 104 rotation speed, in which a y-axis 304 represents IP time width and an x-axis 306 represents rotating gantry rotational speed. As shown in FIG. 3, the IP timing and the IP error decrease with increasing rotating gantry rotation speed. As such, the IP timing error determiner 204 and the IP timing corrector 206 can be used, omitted or not utilized at higher rotation speeds, and utilized at lower rotation speeds to correct for IP error.

In another variation, the IP error values for a scanner are determined ahead of time, for example, during a calibration or other procedure, and stored in a table such as a look up table (LUT) with the scanner. In this instance, LUT can be utilized by the IP timing corrector 206 to correct the IP timing signal from the IP timing predictor 202.

In another variation, an adaptive error calculation algorithm could be used for non-stationary errors. This would be useful, for example, if an unpredicted disturbance occurs in the system such as a varying imbalance or motor torque corrections during an acquisition.

In another variation, a standard motor encoder can be utilized to drive the rotating gantry at a constant velocity, which may compensate or reduce imbalance torque, which may reduce the IP timing error.

In another variation, a one cycle per revolution magnitude and phase of the motor current could be used to measure the IP inaccuracy and improve IP timing similar to and possibly in conjunction with additional position sensors as described above. The torque could be used after an acquisition has been made to improve the timing.

FIGS. 4 and 5 illustrate a non-limiting example in which the IP timing error determiner 204 and the IP timing corrector 206 are omitted or not utilized.

Initially referring to FIG. 4, a sensor 402 is affixed to the rotating gantry 104 and a flag 404 is affixed to the stationary gantry 102. The sensor 402 and the flag 404 are arranged with respect to each other such that the sensor 402 rotates passed the flag 404 each revolution of the rotating gantry 104. The sensor 402 is configured to detect the flag 404 as the sensor 402 rotates passed the flag 404 and generate an output signal indicative thereof.

FIG. 5 shows an example output of the sensor 402. In FIG. 5, an x-axis 502 represents time and a y-axis 504 represents the output of the sensor 402. An output signal 506 represents the output of the sensor 402. With respect to the output signal 506, a first output pulse 508 corresponds to the sensor 402 passing the flag 404 for a revolution, and a second output pulse 510 corresponds to the sensor 402 passing the flag 404 for a next revolution.

With continuing reference to FIGS. 4 and 5, the gantry revolution information determiner 120 includes a timer 406. In this example, the timer 406 resets and begins timing a revolution on the rising edge of the pulse 508. On the rising edge of the subsequent pulse 510, the timer 406 provides a time signal 516, which is indicative of the time of the revolution, to the IP timing predictor 202, and the timer 406 is reset and begins timing the next revolution.

The IP timing predictor 202 determines the IP timing signal for the next revolution as described above, for example, by dividing the time signal 516 by the number of IPs and the rotating gantry 104 rotation speed for the next revolution, which can be obtained from the console 124 or otherwise. The IP timing signal is provided to the IP pulse generator 208, which utilizes the IP timing signal to generate integrator 116 reset pulses for the revolution.

A non-limiting implementation may include a counter, which is triggered by the output of the sensor 402 and which determines a time duration of a revolution, a latch, which is also triggered by the output of the sensor 402 and which holds the IP timing signal (which is calculated by dividing the time duration by the product of the number of IPs and the rotation speed), and a timer, which produces a serial stream of trigger pulses based on the IP timing signal. A summer can be incorporated before the timer to add a IP error correction signal to the IP timing signal.

FIGS. 6 and 7 illustrate a non-limiting example in which the IP timing error determiner 204 and the IP timing corrector 206 are utilized to correct the predicted IP timing signal. Recall that at lower rotation speeds, the predicted IP timing signal may need to be corrected for variations in angular position, for example, due to gantry imbalance and/or otherwise.

Initially referring to FIG. 6, at least a first sensor 602 and a second sensor 604 are affixed to the rotating gantry 104 and at least a first flag 606 and a second flag 608 are affixed to the stationary gantry 102 (or rotating gantry 104). The at least two flags 606 and 608 are angularly offset from each other by an angular distance (α) 610. In the illustrated embodiment, α is about ninety degrees. The at least two sensors 602 and 604 are angularly offset from each other by an angular distance (β) 612. In the illustrated embodiment, β is about one hundred and eighty degrees.

It is to be understood that the illustrated embodiment is non-limiting. In other embodiments, there may be more or less sensors and/or flags, and the location of the sensors and/or flags with respect to each other and the rotating and/or stationary gantries can be different.

FIG. 7 shows an example output of the sensors 602 and 604. In FIG. 7, an x-axis 702 represents time and a y-axis 704 represents the output of the at least sensors 602 and 604. A first output signal 706 represents the output of the sensor 602 (or sensor 604), and a second output signal 708 represents the output of the sensor 604 (or sensor 602).

With respect to the output signal 706, a first output pulse 710 corresponds to the first sensor 602 passing the first flag 606, and a second output pulse 712 corresponds to the first sensor 602 passing the second flag 608. With respect to the output signal 708, a first output pulse 714 corresponds to the second sensor 604 passing the first flag 606, and a second output pulse 716 corresponds to the second sensor 604 passing the second flag 608. The pulse 711 corresponds to the first sensor 602 passing the first flag 606 for a subsequent revolution.

In this example, and similar to the example of FIGS. 4-6, the timer 406 is used to determine a time duration 718 of a revolution based on the time difference between the pulse 710 and the pulse 711. The timer 406 also can be used to determine a time distance 720 between the flags 606 and 608 based on the time difference between the pulses 710 and pulse 712, and a time distance 722 between the sensor 602 and 604 based on the difference between the pulses 714 and pulse 716.

In the illustrated embodiment, the flag 606 is assigned as a reference angular position of zero (0). The angular distance ($\alpha$) between the flag 606 and the flag 608 can be determined as the quotient of the time distance 720 between the flags 606 and 608 and the time distance 718 of one revolution. The angular distance ($\beta$) between the sensors 602 and 604 can be determined as the quotient of the time distance 722 between the sensors 602 and 604 passing the flag 608 and the time distance 718 of one revolution. The angular distance between the sensor 602 passing the flag 606 and the sensor 604 passing the flag 608 can be determined through summing the angular distances $\alpha$ and $\beta$ ($\alpha+\beta$). The times $\alpha$ and $\beta$ can be referred to as calibrated measurement times, and can be determined by the measurement of the time between flags during the minimal disturbance condition, which is usually during rotor maximum speed.

The IP timing error determiner 204 (FIG. 2) can determine an IP error for the predicted IP timing signal based on the predicted IP timing and the measured IP timing 718-722 for the angular positions 0, $\alpha$, $\beta$ and $\alpha+\beta$ as shown in EQUATION 1:

$$\hat{T}_{predicted} - \hat{T}_{measured} = I\sin(\Theta+\Phi) + \overline{E} \quad \text{EQUATION 1:}$$

wherein $\Theta$ represents the angular positions 0, $\alpha$, $\beta$ and $\alpha+\beta$, $\hat{T}_{predicted}$ represents predicted IP timing for the angular positions $\Theta$, $\hat{T}_{measured}$ represents measured timing for the angular positions $\Theta$, I is an unknown and represents the inertial amplitude Mo/J$\omega^3$, where Mo represents the static imbalance, J represents the rotor inertia about the rotation axis z, and $\omega$ represents the rotation speed, $\Phi$ is an unknown and represents the phase of the imbalance, and $\overline{E}$ represents the average of $\hat{T}_{ideal} - \hat{T}_{measured}$.

Using the trigonometric identity $I\sin(\Theta+\Phi) = I\cos\Phi\sin\Theta + I\sin\Phi\cos\Theta$, and defining $\gamma=I\cos\Phi$, $\sigma=I\sin\Phi$; $S=\sin(\Theta)$; $C=\cos\Theta$, and $Y=\hat{T}_{predicated}-\hat{T}_{measured}-\overline{E}$, EQUATION 1 can be re-written as shown in EQUATION 2:

$$Y = S\gamma + C\sigma, \quad \text{EQUATION 2:}$$

wherein $\gamma$ and $\sigma$ are unknowns. Multiplying EQUATION 2 by the transpose of S (i.e., $S^t$) and by the transpose of C (i.e., $C^t$) respectfully results in EQUATIONS 3 and 4:

$$C^tY = C^tS\gamma + C^tC\sigma, \text{ and} \quad \text{EQUATION 3:}$$

$$S^tY = S^tS\gamma + S^tC\sigma, \quad \text{EQUATION 4:}$$

or, two equations with two unknowns, which can be solved via simultaneous equations. In matrix form, EQUATIONS 3 and 4 can be represented as shown in EQUATIONS 5 and 6:

EQUATION 5:

$$\begin{bmatrix} S^tS & S^tC \\ C^tS & C^tC \end{bmatrix}\begin{pmatrix} \gamma \\ \sigma \end{pmatrix} = \begin{pmatrix} S^tY \\ C^tY \end{pmatrix} \text{ and}$$

EQUATION 6:

$$\begin{pmatrix} \gamma \\ \sigma \end{pmatrix} = \begin{bmatrix} S^tS & S^tC \\ C^tS & C^tC \end{bmatrix}^{-1}\begin{pmatrix} S^tY \\ C^tY \end{pmatrix},$$

which can be solved for $\gamma$ and $\sigma$.

From $\gamma$ and $\sigma$ the, unknowns I and $\Phi$ from EQUATION 1 can be determined respectfully from EQUATIONS 7 and 8:

EQUATION 7:

$$I = \sqrt{\gamma^2 + \sigma^2}, \text{ and}$$

EQUATION 8:

$$\Phi = \tan^{-1}\left(\frac{\gamma}{\sigma}\right).$$

From above, I represents the inertial amplitude Mo/J$\omega^3$, where Mo represents the static imbalance, J represents the rotor inertia about the rotation axis z, and $\omega$ represents the rotation speed, and can be utilized to determine the IP error as shown in EQUATION 9:

$$E(t)I = (Mo/(J\omega^3))\sin(\omega\tau). \quad \text{EQUATION 9:}$$

Figure 8:
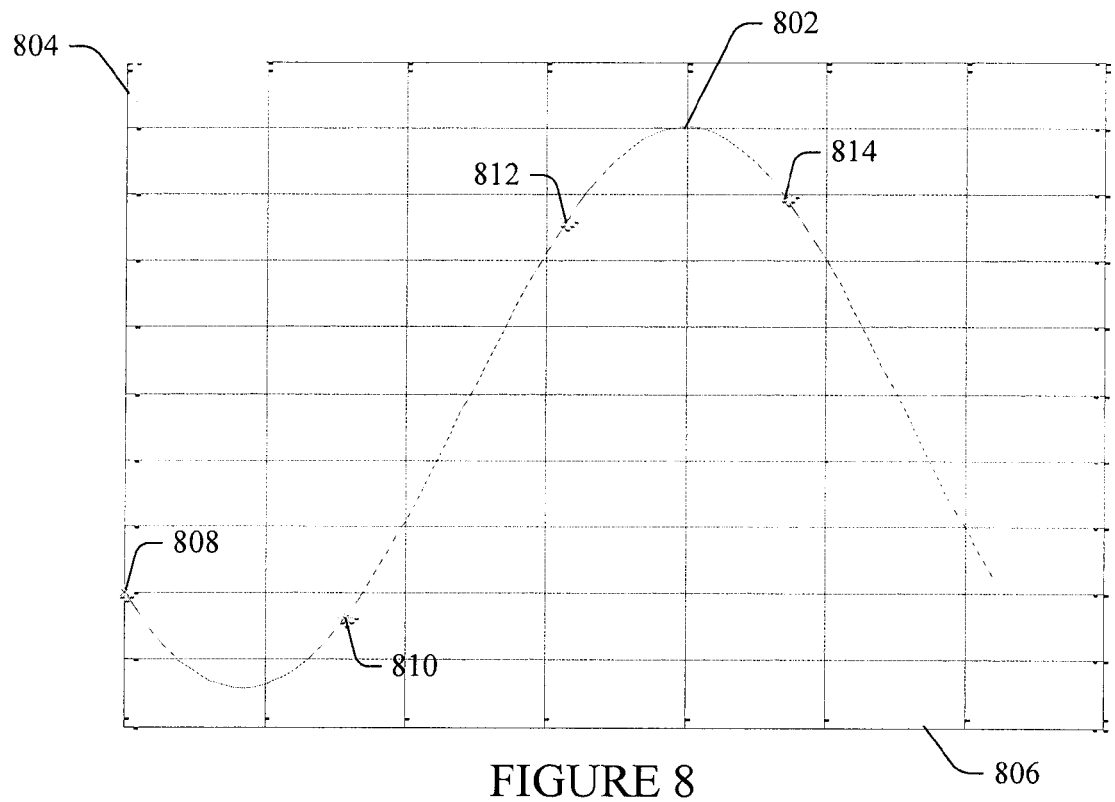
FIG. 8 shows an example error curve representing the IP error as a function of angular position.

FIG. 8 shows an error curve 802 representing the IP error as a function of angular position, in which a y-axis 804 represents the error value (or deviation from the actual angular position) and an x-axis 806 represents the angular position. The points 808, 810, 812 and 814 correspond to the angular positions $\Theta$ (or 0, $\alpha$, $\beta$ and $\alpha+\beta$). The error curve 802 is fitted to the points 808, 810, 812 and 814. At the point 808, the initial IP angular position for a revolution, the IP angular position error is zero (0). The error at a given angular range can be determined by deviation in error with respect to the value at point 808.

The IP timing error determiner 204 provides the IP timing error curve to the IP timing corrector 206, which utilizes the IP timing error curve to correct the predicted IP timing signal predicted by the IP timing predictor 202. By way of example, in one non-limiting instance, the IP timing corrector 206 adds the IP timing error curve to the IP timing signal, which shifts the IP timing to that the IPs are synchronized with rotating gantry angular position.

It is to be appreciated that using additional sensors and/or flags may improve the imbalance error estimation. For example, using additional sensors and/or flags may reduce noise. Depending on the number of sensors and/or flags, the IP controller 118 may behave substantially similar to a high resolution encoder.

Figure 9:
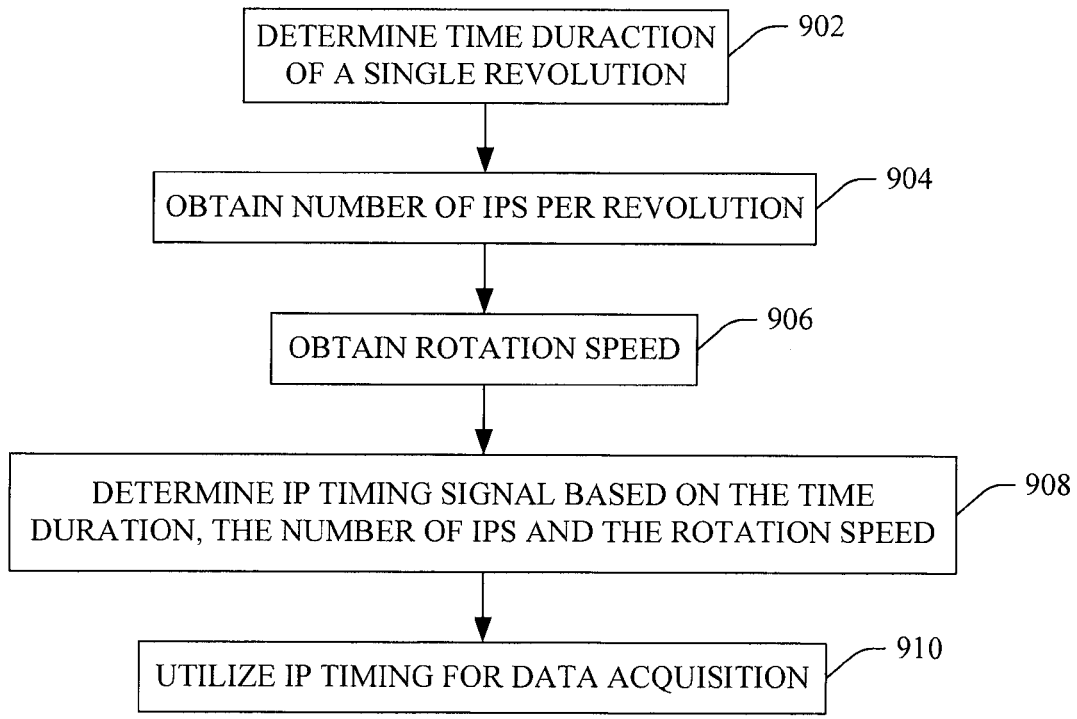
FIG. 9 illustrates an example method for determining an IP timing signal.

FIG. 9 illustrates an example method for determining an IP timing signal.

It is to be appreciated that the ordering of the acts in the methods described herein is not limiting. As such, other orderings are contemplated herein. In addition, one or more acts may be omitted and/or one or more additional acts may be included.

At 902, a time duration of a revolution of the rotating gantry 104 is determined. As described herein, this can be achieved through a sensor, a flag, and a timer.

At 904, the number of IPs for one or more subsequent revolutions is obtained.

At 906, the rotating gantry rotation speed for the one or more subsequent revolutions is obtained.

At 908, an IP timing signal for the subsequent one or more subsequent revolutions is determined by dividing the revolution time by the product of the number of IPs and the rotating gantry rotation speed.

At 910, the IP timing signal is utilized during data acquisition to determine the IPs during at least one of the one or more subsequent revolutions.

Figure 10:
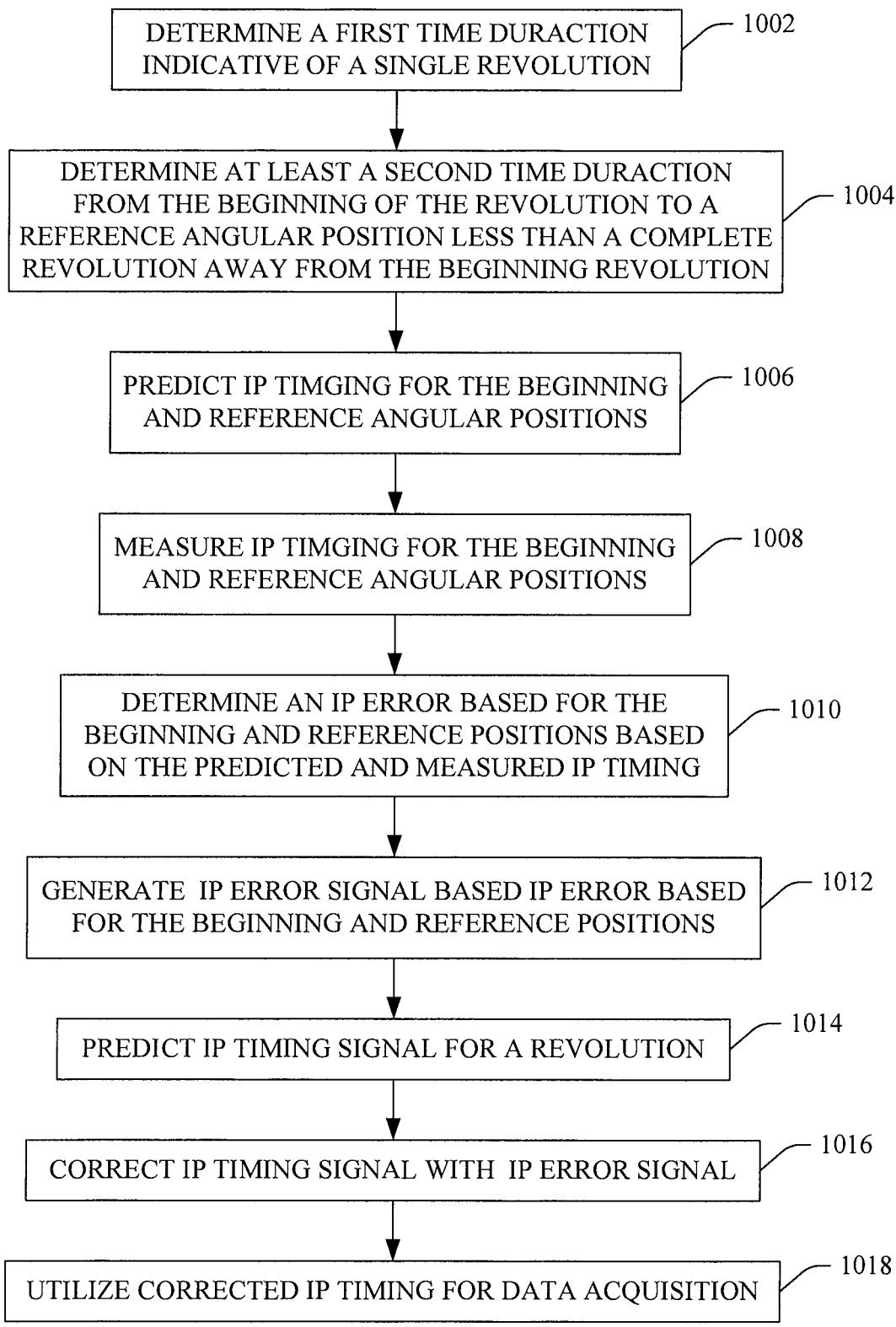
FIG. 10 illustrates an example method for determining a gantry imbalance corrected IP timing signal.

FIG. 10 illustrates an example method for determining a corrected IP timing signal.

It is to be appreciated that the ordering of the acts in the methods described herein is not limiting. As such, other orderings are contemplated herein. In addition, one or more acts may be omitted and/or one or more additional acts may be included.

At 1002, a first time duration of a revolution of the rotating gantry 104 is determined, as described herein.

At 1004, at least a second time duration from a beginning angular position of the revolution to at least a first reference angular position, which is less than a complete revolution ($2\pi$) away from the beginning angular position, is determined. As described herein, this can achieved through sensors, flags, and a timer.

Ay 1006, IP timing is predicted for the reference angular position.

Ay 1008, IP timing is measured for the reference angular position.

Ay 1010, IP timing error is determined based on a difference between the predicted and measured angular positions.

Ay 1012, an IP error signal is generated by fitting the error values at the beginning angular position and the at least first reference angular position to a curve covering the revolution.

At 1014, an IP timing signal for one or more subsequent revolutions is determined based on the first time duration, and a number of IPs and a rotation speed for the subsequent revolution.

At 1016, the IP timing signal is corrected based on the IP error signal. As described herein, this can be achieved by summing the signals.

At 1018, the corrected IP timing signal is utilized during data acquisition to determine the IPs during at least one of the one or more subsequent revolutions.

The above may be implemented by way of computer readable instructions, which when executed by a computer processor(s), cause the processor(s) to carry out the described acts. In such a case, the instructions are stored in a computer readable storage medium associated with or otherwise accessible to the relevant computer.

The invention has been described herein with reference to the various embodiments. Modifications and alterations may occur to others upon reading the description herein. It is intended that the invention be construed as including all such modifications and alterations insofar as they come within the scope of the appended claims or the equivalents thereof.

What is claimed is:

1. An imaging system, comprising:
   a stationary gantry;
   two or more flags affixed to the stationary gantry and angularly offset from each other by a first angle;
   a rotating gantry rotatably supported by the stationary gantry and configured to rotate around an examination region;
   two or more sensors affixed to the rotating gantry and angularly offset from each other by a second angle, wherein the two or more sensors respectively detect a flag in response to rotating passed the flag and generate an output signal indicative thereof
   a radiation source, carried by the rotating gantry, that is configured to emit radiation that traverses the examination region;
   a detector array, carried by the rotating gantry and located opposite the radiation source across the examination region, that detects radiation that traverses the examination region, wherein the detector array detects radiation for a plurality of integration periods during a rotating gantry revolution, wherein the plurality of integration periods corresponds to different angular position ranges, and wherein the detector array generates a signal indicative of the detected radiation respectively for the plurality of integration periods;
   a timer that determines time durations between two flags and/or two sensors; and
   an integration period controller that generates an integration period timing signal that includes timing for a start of each of the integration periods for a revolution of the rotating gantry based at least on the time durations, which include a time duration of a previous revolution of the rotating gantry around the examination region, wherein the integration timing signal is used to trigger the plurality of integration periods, wherein the integration period controller generates an integration period error signal and corrects the integration period timing signal based on the integration error signal and an integration period timing error curve.

2. The imaging system of claim 1, wherein the integration period controller determines the integration period timing signal by dividing the time duration of the previous revolution by a product of a number of integration periods and a rotating gantry rotation speed for the subsequent revolution.

3. The imaging system of claim 1, wherein the integration period controller corrects the integration period timing signal by summing the integration period timing signal and the integration error signal.

4. The imaging system of claim 1, wherein the integration period error signal is indicative of fluctuations in rotating gantry velocity during the revolution.

5. The imaging system of claim 1, wherein the integration period error signal is indicative of rotating gantry imbalance.

6. The imaging system of claim 1, further comprising:
   an integration period timing error determiner that determines timing errors for two or more angular positions of the rotating gantry based on a difference between predicted integration period timing for the two or more angular positions of the rotating gantry and measured integration period timing for the two or more angular positions of the rotating gantry.

7. The imaging system of claim 4, wherein two or more angular positions of the rotating gantry are determined by dividing corresponding time durations by the time duration of the revolution.

8. The imaging system of claim 6, wherein the integration period timing error determiner determines the integration period error signal by fitting the timing errors for the two or more angular positions of the rotating gantry to the integration period timing error curve.

9. A method, comprising:
   transmitting radiation, with a radiation source, that traverses an examination region, wherein the radiation source is carried by a rotating gantry that is rotatably supported by a stationary, gantry and is configured to rotate around the examination region;

detecting, with a detector array, radiation that traverses the examination region, wherein the detector array detects radiation for a plurality of integration periods during a rotating gantry revolution, wherein the plurality of integration periods corresponds to different angular position ranges, wherein the detector array generates a signal indicative of the detected radiation respectively for the plurality of integration periods, and wherein the detector array is carried by the rotating gantry and is located opposite the radiation source across the examination region:

determining, with a timer, time durations between at least one of two flags affixed to the stationary gantry and angularly offset from each other by a first angle or two sensors affixed to the rotating gantry and angularly offset from each other by a second angle, wherein the two or more sensors respectively detect a flag in response to rotating passed the flag and generate an output signal indicative thereof;

generating, with an integration period controller, an integration period timing signal including timing for a start of each of the integration periods for a revolution of the rotating gantry, wherein the integration period timing signal is generated based at least on the time durations, which include a time duration of a previous revolution of the rotating gantry around the examination region, and wherein the integration timing signal is used to trigger the plurality of integration periods:

generating, with the integration period controller, an integration position error signal; and correcting, with the integration period controller, the integration period timing signal based on the integration error signal and an integration period timing error curve.

10. The method of claim 9, further comprising:

generating the integration period timing signal by dividing the time durations by a number of the integration periods and a rotating gantry rotation speed.

11. The method of claim 9, further comprising:

correcting the integration period timing signal by summing the integration period timing signal and the integration position error signal.

12. The method of claim 9, further comprising:

predicting integration period timing for a plurality of angular locations;

measuring integration period timing for the plurality of angular locations; and determining integration period positioning errors for the plurality of angular locations.

13. The method of claim 12, further comprising:

generating the integration position error signal based on the determined integration period positioning errors for the plurality of angular locations.

14. The method of claim 9, wherein the integration period error signal is indicative of fluctuations in rotating gantry velocity during the revolution.

15. The method of claim 9, wherein the integration period error signal is indicative of rotating gantry imbalance.

* * * * *